(12) United States Patent
Kim et al.

(10) Patent No.: US 11,938,203 B2
(45) Date of Patent: Mar. 26, 2024

(54) OIL-DISPERSED COMPOSITION AND COSMETICS FOR LIP CARE USING THE SAME

(71) Applicant: AMOREPACIFIC CORPORATION, Seoul (KR)

(72) Inventors: Minjeong Kim, Yongin-si (KR); Jinhee Jo, Yongin-si (KR); Minkyung Shim, Yongin-si (KR)

(73) Assignee: AMOREPACIFIC CORPORATION, Seoul (KR)

(*) Notice: Subject to any disclaimer, the term of this patent is extended or adjusted under 35 U.S.C. 154(b) by 0 days.

(21) Appl. No.: 17/646,794

(22) Filed: Jan. 3, 2022

(65) Prior Publication Data
US 2022/0265526 A1 Aug. 25, 2022

(30) Foreign Application Priority Data
Feb. 19, 2021 (KR) .................. 10-2021-0022786

(51) Int. Cl.
*A61K 8/04* (2006.01)
*A61K 8/37* (2006.01)
*A61Q 19/00* (2006.01)

(52) U.S. Cl.
CPC .................. *A61K 8/04* (2013.01); *A61K 8/37* (2013.01); *A61Q 19/001* (2013.01); *A61K 2800/31* (2013.01)

(58) Field of Classification Search
None
See application file for complete search history.

(56) References Cited

U.S. PATENT DOCUMENTS

2009/0280077 A1* 11/2009 Yoshida ................. A61K 8/442
424/59

FOREIGN PATENT DOCUMENTS

| CN | 110559200 A | | 12/2019 |
|---|---|---|---|
| JP | 2002-507202 A | | 3/2002 |
| JP | 2004262783 | * | 9/2004 |
| JP | 2006515027 | * | 5/2006 |
| JP | 5070088 | * | 11/2012 |
| KR | 10-2011-0057819 A | | 6/2011 |
| KR | 10-2015-0023844 A | | 3/2015 |
| KR | 10-2017-0025647 A | | 3/2017 |
| KR | 10-2020-0056210 A | | 5/2020 |

OTHER PUBLICATIONS

Happy Eunjin, "The Face Shop Dr. Bellmeur Lip Balm's prime ingredient analysis", Happy Eunjin's Beautiful Life, Naver Blog, 17 pages.

* cited by examiner

*Primary Examiner* — Danah Al-Awadi
(74) *Attorney, Agent, or Firm* — Sughrue Mion, PLLC (57) ABSTRACT

Disclosed are an oil-dispersed composition and a cosmetic for lip care manufactured using the same. The oil-dispersed composition includes a water-soluble raw material, an ester oil including a glyceryl group and/or an isostearyl group, a paste, and a thickener, wherein the paste and thickener are included in an amount of greater than or equal to about 30 wt % based on the total amount of the oil-dispersed composition.

10 Claims, 10 Drawing Sheets

OIL-DISPERSED COMPOSITION AND COSMETICS FOR LIP CARE USING THE SAME

CROSS-REFERENCE TO RELATED APPLICATION

This application claims priority to and the benefit of Korean Patent Application No. 10-2021-0022786 filed in the Korean Intellectual Property Office on Feb. 19, 2021, the entire contents of which are incorporated herein by reference.

BACKGROUND

(a) Field

This disclosure relates to an oil-dispersed composition, a method of applying it to a skin, and a cosmetic for lip care using the same.

(b) Description of the Related Art

Recently, as healthy lips have been increasingly important to secure as the basics of lip makeup, there is a demand for a product that emphasizes a lip-improving function as well as a color and a texture. Even in the field of functional cosmetics, customers' needs for functional cosmetics with excellent effects such as wrinkle relief of lip skin as well as general skin, redness improvement, antioxidation, elasticity improvement, and the like are significantly increasing. In response to this demand, products with excellent effects such as anti-wrinkle, redness improvement, antioxidation, and elasticity in lip cosmetics are planned. In general, lip cosmetics having the aforementioned effects of anti-wrinkle and the like are manufactured by mixing waxy materials with an oil base, and these ingredients may be categorized into a couple of groups as follows.

First, solid ingredients, for example, candelilla wax, ceresin, carnauba wax, paraffin, wood wax, braze, beeswax, microcrystalline wax, synthetic wax, polyethylene, etc. are used to increase hardness and maintain an external form of a cosmetic composition for lips. Secondly, liquid oily ingredients, for example, jojoba oil, squalane, lanolin oil, lanolin derivative, oil extracted from animals and plants, synthetic ester oil, silicone oil, etc. are included. Thirdly, effective raw materials for improving lip conditions, for example, vitamins, high moisturizing ingredients, and antioxidizing components are blended. Fourthly, color ingredients, for example, organic and inorganic pigments are included, and fifthly, other ingredients, for example, oxidation inhibitors, preservatives, fragrances, nutrients, etc. are added In addition, functional ingredients for lip wrinkle improvement may be optionally included. As shown above, the main formulation ingredients for lip cosmetics are oil-soluble, while most of the effective raw materials are water-soluble.

In other words, general lip care products are oil-dispersed formulations and thus difficult to include the effective raw materials. Most of the effective raw materials have water-soluble properties and thus are difficult to apply to an oil-dispersed anhydrous formulation.

On the other hand, since high efficacy products loaded with efficacy in lip care products just like in various skin care products have recently attracted more interests, the effective raw materials need to be stabilized in oil dispersion, and accordingly, research on an oil-dispersed composition capable of stabilizing sparingly soluble effective raw materials is being actively conducted.

SUMMARY

An embodiment provides an oil-dispersed composition capable of stabilizing a sparingly soluble effective material that is difficult to apply to an anhydrous-type oil-dispersed composition.

Another embodiment provides a cosmetic for lip care prepared using the oil-dispersed composition.

According to an embodiment, an oil-dispersed composition includes a water-soluble raw material, an ester oil including a glyceryl group and/or an isostearyl group, a paste, and a thickener, wherein the paste and thickener are included in an amount of greater than or equal to about 30 wt % based on the total amount of the oil-dispersed composition.

The paste may include polybutene, hydrogenated polyisobutene, phytosteryl/isostearyl/cetyl/stearyl/behenyl dimer dilinoleate, dimer dilinoleyl hydrogenated rosinate, or a combination thereof.

The thickener may include an ethylene/propylene/styrene copolymer, a butylene/ethylene/styrene copolymer, dextrin palmitate/ethylhexanoate, glyceryl behenate/eicosadioate, or a combination thereof.

The paste may be included in a larger amount than that of the thickener.

The paste may be included in an amount of greater than or equal to about 25 wt % based on the total amount of the oil-dispersed composition.

The ester oil including the glyceryl group and/or isostearyl group may include polyglyceryl-2 triisostearate, diisostearylmalate, or a combination thereof.

The ester oil may include a glyceryl group-containing ester oil and an isostearyl group-containing ester oil, and the isostearyl group-containing ester oil may be included in a larger amount than the glyceryl group-containing ester oil.

The water-soluble raw material may include thymol trimethoxy cinnamate, vitamins and derivatives thereof, ceramides, or a combination thereof.

The oil-dispersed composition may further include a malic acid derivative.

The oil-dispersed composition may further include waxes, butters, or a combination thereof.

The oil-dispersed composition may further include a hydrocarbon-based oil.

The hydrocarbon-based oil may include hydrogenated poly(C6-14 olefin).

The oil-dispersed composition may include about 0.01 wt % to about 1 wt % of the water-soluble raw material, about 15 wt % to about 69 wt % of the ester oil including the glyceryl group and/or the isostearyl group, about 25 wt % to about 74 wt % of the paste, and about 0.1 wt % to about 10 wt % of the thickener based on the total amount of the oil-dispersed composition.

The oil-dispersed composition may further include tocopherol, evening primrose oil (*Oenothera biennis* oil), or a combination thereof.

The oil-dispersed composition may be a composition for magenta or a composition for improving clarity of lip color.

According to another embodiment, a cosmetic for lip care prepared using the oil-dispersed composition is provided.

According to another embodiment, a method of applying the oil-dispersed composition to the skin is provided.

The oil-dispersed composition according to an embodiment may sufficiently dissolve water-soluble effective raw materials. In addition, the oil-dispersed composition according to an embodiment has a slightly softer formulation compared with the conventional lip care cosmetic composition formulation such as lip balm, and may maintain a high viscosity even at high temperatures, so that dispersion of water-soluble effective raw materials and stability of the formulation may be secured at the same time.

DETAILED DESCRIPTION OF THE EMBODIMENTS

Hereinafter, embodiments of one aspect of the present disclosure will be described in detail, and may be easily performed by a person having ordinary skill in the related art. However, this disclosure may be embodied in many different forms and is not construed as limited to the example embodiments set forth herein.

In the present specification It will be understood that when an element such as a layer, film, region, or substrate is referred to as being "on" another element, it may be directly on the other element or intervening elements may also be present. In contrast, when an element is referred to as being "directly on" another element, there are no intervening elements present.

As used herein, the term "paste" includes not only monomolecular compounds, but also low molecular weight compounds and high molecular weight polymers as a material having both solid and liquid properties.

Hereinafter, an oil-dispersed composition according to an embodiment and a cosmetic for lip care prepared using the same are described.

One aspect of the present disclosure relates to a cosmetic composition for lips that realizes lip efficacy by allowing water-soluble effective raw materials to be well dispersed in an oil-dispersion formulation including a paste and a thickener in a high content (30 wt % or more).

Since most of the conventional cosmetic compositions for lips have an oil-dispersion formulation, when water-soluble effective materials are loaded, there are problems such as stability decrease of the effective materials decreases, solubility decrease of the effective materials, potency decrease of the effective materials in the formulation, and uneven dispersibility of the effective materials.

Accordingly, the present inventors, after undergoing numerous trials and errors, increased stability of the water-soluble effective material in the oil-dispersion formulation by including the paste and thickener in a high content of greater than or equal to about 30 wt % based on the total amount of the oil-dispersed composition, and at the same time, by using an ester oil including a glyceryl group and/or an isostearyl group.

Conventional general lip balm formulations are hard solid or liquid, and thus it is difficult to apply a sufficient amount to the lips. In the case of the liquid form, since it flows easily, it is difficult to put a sufficient amount on the lips and in the case of the solid form, it is too hard to apply a sufficient amount on the lips. Therefore, the conventional lip balm formulation has a disadvantage in that the shielding power is not good. However, according to an embodiment, since the paste and the thickener is included in a high content of greater than or equal to about 30 wt % based on the total amount of the oil-dispersed composition, it has sufficient shielding power, so that the effect of preventing the evaporation of moisture from the lips may be realized. Thereby, it is possible to maximize the efficacy of the water-soluble effective material, which is another ingredient, on the lips.

As for sparingly soluble water-soluble effective materials that are not well dissolved in an oil-dispersed composition, the water-soluble effective material is important to dissolve in the oil-dispersed composition and also important to uniformly disperse in the oil-dispersed composition. Since an oil-dispersed lip composition including waxes, butters, etc. is filled at a high temperature of greater than or equal to about 70° C. (since the composition including waxes, butters, or the like may be formed into a solid, only when filled at a high temperature of greater than or equal to about 70° C.), when the ingredients are sufficiently uniformly dispersed at the temperature, uniform potency of the entire composition may be obtained. In other words, when a formulation has low viscosity at greater than or equal to about 70° C., (even though the water-soluble effective raw materials are well dispersed in the oil-dispersed composition) the water-soluble effective raw materials sink down, causing a non-uniform potency problem during the filling process. In order to solve this non-uniform potency problem, it is important to maintain high viscosity for sufficient dispersion even at a high temperature of greater than or equal to about 70° C., but one embodiment includes a paste and a thickener in a high amount of 30 wt % or more based on the total amount of the oil-dispersed composition and thus maintains high viscosity at a high temperature of greater than or equal to about 70° C. and thus is free from the potency problem.

For example, the paste may include polybutene, hydrogenated polyisobutene, phytosteryl/isostearyl/cetyl/stearyl/behenyl dimer dilinoleate, dimer dilinoleyl hydrogenated rosinate, or a combination thereof.

The thickener may include an ethylene/propylene/styrene copolymer, a butylene/ethylene/styrene copolymer, dextrin palmitate/ethyl hexanoate, glyceryl behenate/eicosadioate, or a combination thereof.

When the paste and the thickener are as described above, it may be more advantageous to maintain a high viscosity even at a high temperature of greater than or equal to about 70° C., and at the same time may not impair the moisturizing power.

For example, the paste may be included in an amount greater than that of the thickener. For example, the paste may be included in an amount of greater than or equal to about 25 wt % based on the total amount of the oil-dispersed composition according to an embodiment.

The ester oil including the glyceryl group and/or isostearyl group stabilizes a water-soluble effective ingredient known to be sparingly soluble. When an ester oil that does not include a glyceryl group and/or an isostearyl group is used, the sparingly soluble water-soluble effective ingredient may be eluted from the oil-dispersion formulation.

For example, the ester oil including the glyceryl group (glyceryl-based ester oil) may include polyglyceryl-2 triisostearate, but is not necessarily limited thereto.

For example, the ester oil including the isostearyl group may be a diester-based oil, and may include, for example, diisostearyl malate, but is not necessarily limited thereto.

For example, when the ester oil includes both glyceryl group-containing ester oil and isostearyl group-containing ester oil, the isostearyl group-containing ester oil may be included in an amount greater than that of the glyceryl group-containing ester oil.

For example, the water-soluble raw material may include thymol trimethoxycinnamate, vitamins and derivatives thereof, ceramides, or a combination thereof, but is not necessarily limited thereto.

As long as the water-soluble raw materials can be well stabilized in the oil-dispersion formulation, a very excellent effect, specifically, the magenta effect (clear redness) of the lips by preventing pigmentation of the lips by melanin pigment may be implemented, clarity of lip color may be increased, and effects such as antioxidation and elasticity and the effect of strengthening the skin barrier of the lips may be realized compared to the conventional oil-dispersion cosmetic composition for lip care. The magenta effect of the lips or the clarity of the lip color may mean that the original lip color is well revealed, which can be confirmed experimentally by comparing the redness or saturation of the lips before and after application of the oil-dispersed composition.

For example, the oil-dispersed composition according to an embodiment may be an oil-dispersed composition for magenta or an oil-dispersed composition for enhancing the clarity of lip color.

For example, an embodiment may provide a method of implementing the magenta effect of the lips by applying the oil-dispersed composition to the lips.

For example, an embodiment may provide a method of increasing the clarity of lip color by applying the oil-dispersed composition to the lips.

For example, an embodiment provides a method of applying the oil-dispersed composition to the lips to realize the magenta effect of the lips or to increase the clarity of lip color, while simultaneously strengthening the skin barrier of the lips, and providing antioxidation and elasticity to the lips.

The thymol trimethoxy cinnamate has excellent compatibility with an ester oil and a silicone-based oil that do not contain a glyceryl group or an isostearyl group in addition to the ester oil containing the glyceryl group and/or the isostearyl group, but has poor compatibility with a hydrocarbon oil-based oil or an alcohol-based oil. In addition, the vitamin derivative and ceramides have few oils with excellent compatibility compared to the thymol trimethoxy cinnamate. For example, the vitamin derivatives and ceramides have poor compatibility with an ester oil and a silicone oil that do not contain a glyceryl group or an isostearyl group. On the other hand, the vitamin derivative has excellent compatibility with an alcohol-based oil, which is in contrast to thymol trimethoxy cinnamate and ceramides.

That is, even for water-soluble effective raw materials, oils with excellent compatibility are different depending on the type, and water-soluble effective raw materials also have different functions depending on the type. Therefore, it is very difficult to prepare an oil-dispersed cosmetic composition for lip care that can implement a specific function. (See Table 1)

Figure 1:
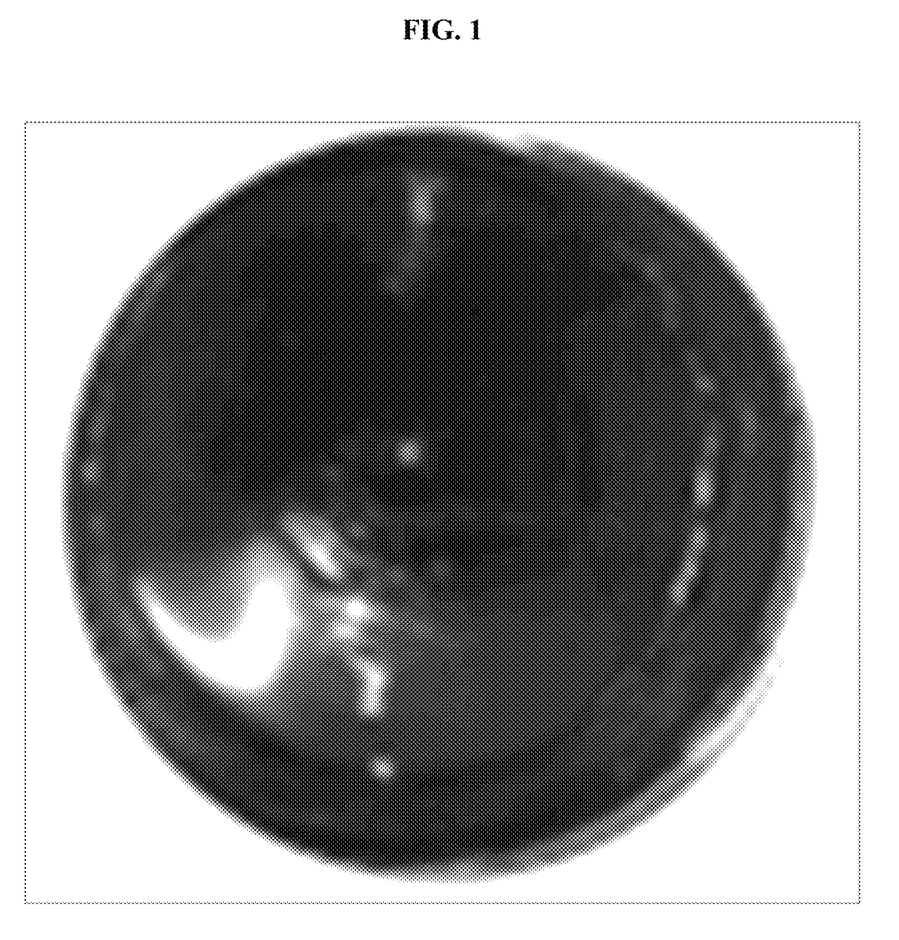
FIG. 1 is a photograph showing that a water-soluble effective raw material, thymol trimethoxy cinnamate is dissolved in diisostearyl maleate.
Figure 2:
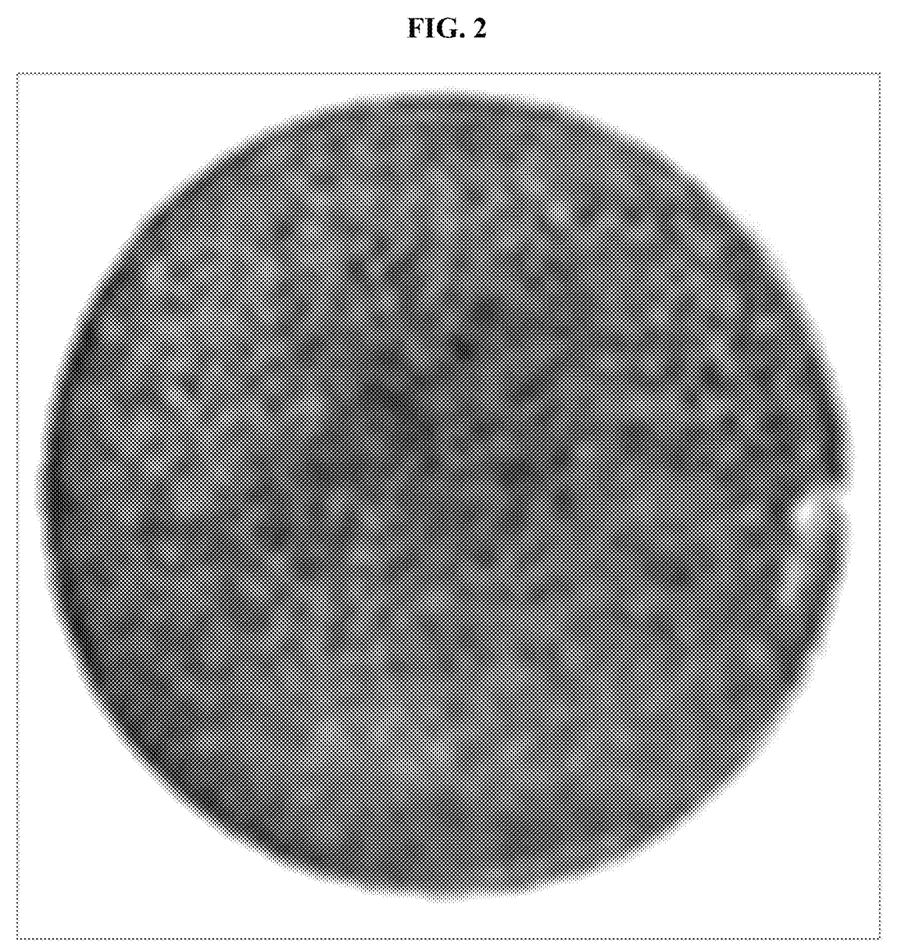
FIG. 2 is a photograph showing that the water-soluble effective raw material, thymoltrimethoxycinnamate is dissolved in pentaerythrityl tetraisostearate.

Referring to FIGS. 1 and 2, thymol trimethoxy cinnamate that is a water-soluble effective raw material has very good compatibility with diisostearyl malate oil that is a diester-based oil (FIG. 1), while it has very poor compatibility with pentaerythrityl tetraisostearate oil that is another ester-based oil (FIG. 2).

However, an embodiment, as described above, solves the aforementioned problem by using an ester oil including a glyceryl group and/or an isostearyl group, for example, using both the glyceryl group-containing ester oil and the isostearyl group-containing ester oil but limiting a structure and a composition of the ester oil, so that the isostearyl group-containing ester oil may be more included than the glyceryl group-containing ester oil.

TABLE 1

| | Water-soluble effective raw materials | | |
| --- | --- | --- | --- |
| Types of oil | Thymol trimethoxy cinnamate | Vitamin derivatives | Ceramides |
| Isononyl isononanoate | O | X | X |
| Octyldodecyl neopentanoate | O | X | X |
| Diisostearyl Malate | O | O | O |
| Pentaerythrityl tetraisostearate | X | X | X |
| Polyglyceryl-2 Triisostearate | O | O | O |
| Hydrogenated poly(C6-14 olefin) | X | X | X |
| Diphenylsiloxy Phenyl Trimethicone | O | X | X |
| Octyldodecanol | X | O | X |
| Butylene glycol | X | O | X |

Compatibility Between Water-Soluble Effective Raw Materials and Oils
  O: Good compatibility
  X: Poor compatibility For example, the oil-dispersed composition may further include a malic acid derivative. The malic acid derivative boosts lip keratin care by lowering the pH of the lips, thereby maximizing the cosmetic effect of the lips due to exfoliation of dead skin cells.

For example, the malic acid derivative may include diisostearyl malate, dioctyldodecyl malate, diisoamyl malate, or a combination thereof, but is not necessarily limited thereto.

Meanwhile, tocopherol, evening primrose oil (*Oenothera biennis* oil), or a combination thereof together with or separately from the malic acid derivative may be further included in the oil-dispersed composition. Both the tocopherol and evening primrose oil may help maximize the cosmetic effect of the lips.

For example, the oil-dispersed composition may further include waxes, butters, or a combination thereof. When the waxes and/or butters are included, the oil-dispersed composition may be more easily prepared.

For example, the oil-dispersed composition may further include a hydrocarbon-based oil.

For example, the hydrocarbon-based oil may further include hydrogenated poly(C6-14olefin).

For example, the oil-dispersed composition may include about 0.01 wt % to about 1 wt % of the water-soluble raw material, about 15 wt % to about 69 wt % of the ester oil including the glyceryl group and/or the isostearyl group, about 25 wt % to about 74 wt % of the paste, and about 0.1 wt % to about 10 wt % of the thickener based on the total amount of the oil-dispersed composition. For example, the thickener may be included in an amount of about 0.1 wt % to about 5 wt %, for example about 5 wt % to about 10 wt % based on the total amount of the oil-dispersed composition. When the oil-dispersed composition has the aforementioned composition, the water-soluble raw materials may be easily dissolved and dispersed in the oil-dispersion formulation and well maintain high viscosity at a high temperature of greater than or equal to about 70° C.

The oil-dispersed composition according to an embodiment may contain various suitable bases and additives as needed, and types and amounts of these ingredients may be easily determined by the inventor. If necessary, the oil-dispersed composition may contain acceptable additives, for example, additionally include ingredients such as preservatives, fragrances, colors, powders, other additives, and the like, which are conventional in the art. For example, the preservatives may be specifically phenoxyethanol, 1,2-hexanediol, or the like, and the fragrances may be artificial fragrances and the like.

In addition, the other additives added thereto are not limited thereto but may be blended within a range that has no damage on the purpose and effect of one aspect of the present disclosure.

Another embodiment provides a cosmetic for lip care prepared using the oil-dispersed composition.

The cosmetic for lip care, unlike a conventional formulation such as a lip balm, etc., has a softer and hand-scooping formulation and includes the water-soluble effective raw materials with high stability and thus exhibit no potency deterioration, when applied to the lips, and accordingly, may be applied before bedtime and kept during the sleep as well as during activity. Since the conventional composition for lip care such as a lip balm and the like does not contain the water-soluble effective raw materials with high stability, the water-soluble effective raw materials are easily precipitated or eluted and thus deteriorate completeness of products, but since the oil-dispersed composition according to an embodiment includes the water-soluble effective raw materials with high stability (has high formulation stability and thus stably includes the water-soluble effective raw materials), when the oil-dispersed composition is applied to lips immediately before bedtime, the water-soluble effective raw materials may be boosted during the sleep and thus provide effective care for the lips, which has rarely been used before and is distinguished from the conventional lip care cosmetics.

For example, the cosmetic for lip care, when about four times applied to artificial leather, may be laminated to have a thickness of greater than or equal to about 60 μm, for example, greater than or equal to about 70 μm, for example, greater than or equal to about 80 μm, for example, greater than or equal to about 90 μm, or for example, greater than or equal to about 100 μm and for example, less than or equal to about 150 μm, for example, less than or equal to about 140 μm, for example, less than or equal to about 130 μm, for example, less than or equal to about 120 μm, or for example, less than or equal to about 110 μm. In other words, since only about 4 times applications form a sufficient thickness on the lips and put the water-soluble effective raw materials on the lips, sufficient lip care effects may be achieved with only a small number of applications. Conventional hard solid lip balm products may not achieve a thickness of about 60 μm or more, for example, a lamination thickness of about 100 μm with only the 4 times applications, which is too thin to secure the lip care effect of the water-soluble effective raw materials. Even though the thickness of about 60 μm or more is achieved with the 4 times applications, the conventional cosmetics may easily flow down from the lips and fail in providing the lip care effect of the water-soluble effective raw materials, but according to an embodiment, since applied on the lips to have a thickness of about 60 μm or more, for example, about 100 μm with only 4 times applications, the lip care effect may be sufficiently achieved by the water-soluble effective raw materials.

Hereinafter, the contents of one aspect of the present disclosure will be described in more detail through examples and comparative examples. These examples are only presented to understand the content of one aspect of the present disclosure, and the scope of one aspect of the present disclosure is not limited to these examples and experimental example. Modifications, substitutions, insertions, etc. commonly known in the art may be performed, and these are also included in the scope of one aspect of the present disclosure.

Preparation of Oil-Dispersed Composition

Each oil-dispersed composition according to Examples 1 and 2 and Comparative Examples 1 to 3 was prepared to have compositions and contents shown in Table 2.

TABLE 2

(unit: wt %)

| Ingredients | Example 1 | Example 2 | Comparative Example 1 | Comparative Example 2 | Comparative Example 3 |
| --- | --- | --- | --- | --- | --- |
| Synthetic wax | 3 | 3 | 8 | 3 | 3 |
| Microcrystalline wax | 3 | 3 | 3 | 3 | 3 |
| Candelilla wax | 1 | 1 | 1 | 1 | 1 |
| Butters | 3 | 3 | 3 | 3 | 3 |
| Polybutene | 15 | 15 | 9 | 15 | — |
| Phytosteryl/isostearyl/cetyl/stearyl/behenyl dimer dilinoleate | 15 | 15 | 9 | 15 | — |
| Hydrogenated polyisobutene*ethylene/propylene/styrene copolymer*butylene/ethylene/styrene copolymer | 20 | — | 9 | — | — |
| Hydrogenated polyisobutene | — | 19.6 | — | 17.5 | — |

TABLE 2-continued (unit: wt %)

| Ingredients | Example 1 | Example 2 | Comparative Example 1 | Comparative Example 2 | Comparative Example 3 |
|---|---|---|---|---|---|
| Dextrin palmitate/ethylhexanoate | — | — | — | 2.5 | — |
| Glyceryl behenate/eicosadioate | — | 0.4 | — | — | — |
| Polyglyceryl-2 triisostearate | 10 | 10 | 20 | 10 | 10 |
| Diisostearylmalate | 15 | 15 | 20 | 15 | 15 |
| Hydrogenatedpoly (C6-14olefin) | To 100 | To 100 | To 100 | To 100 | To 100 |
| Thymol trimethoxy cinnamate | 0.1 | 0.1 | 0.1 | 0.1 | 0.1 |
| Ethyl ascorbyl ether | 0.1 | 0.1 | 0.1 | 0.1 | 0.1 |
| Ceramide NP | 0.1 | 0.1 | 0.1 | 0.1 | 0.1 |
| Preservative | 0.1 | 0.1 | 0.1 | 0.1 | 0.1 |
| Powder (mica) | 4 | 4 | 4 | 4 | 4 |

Evaluation 1: Measurement of Application Thickness

Figure 3:
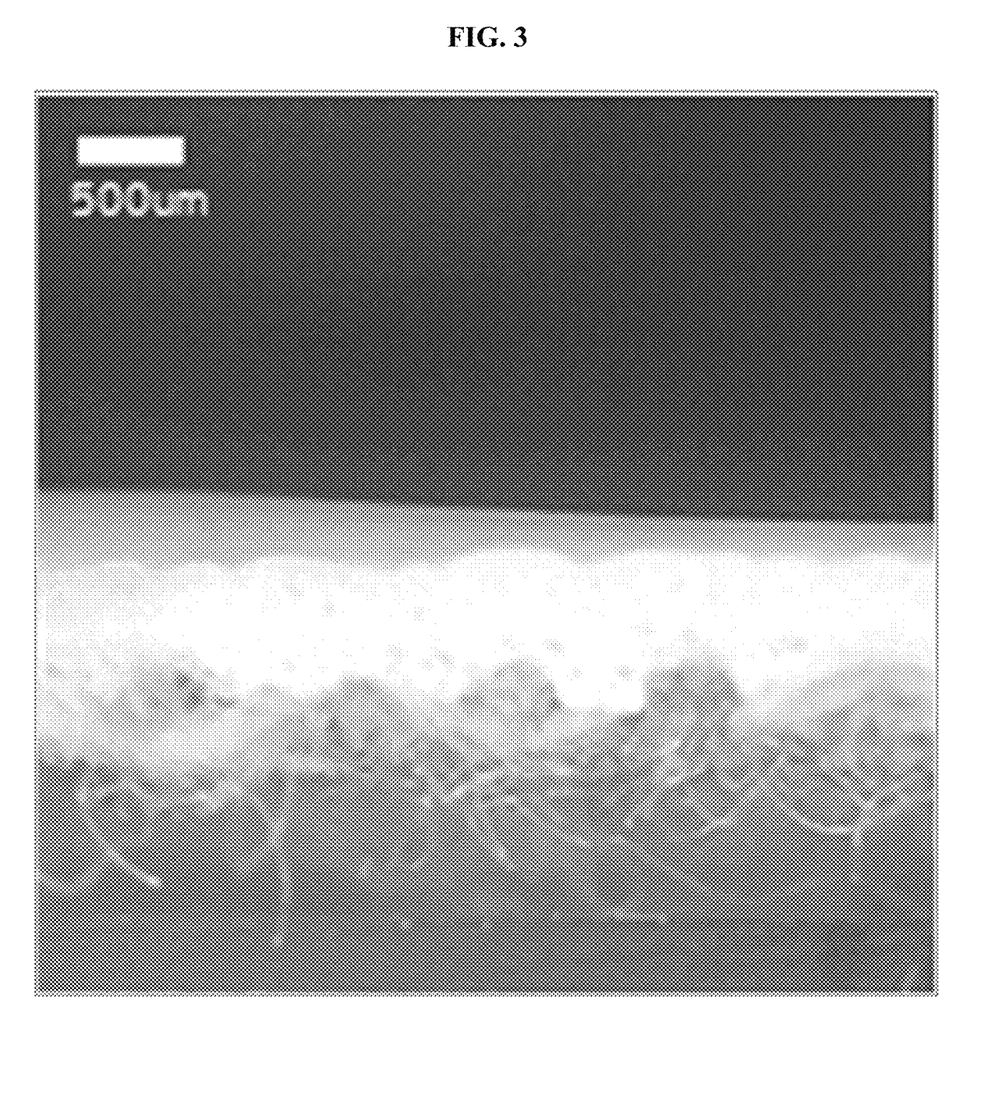
FIG. 3 is a magnified photograph showing that the oil-dispersed composition according to Example 1, which is applied to artificial leather four times, and then the application thickness is measured.
Figure 4:
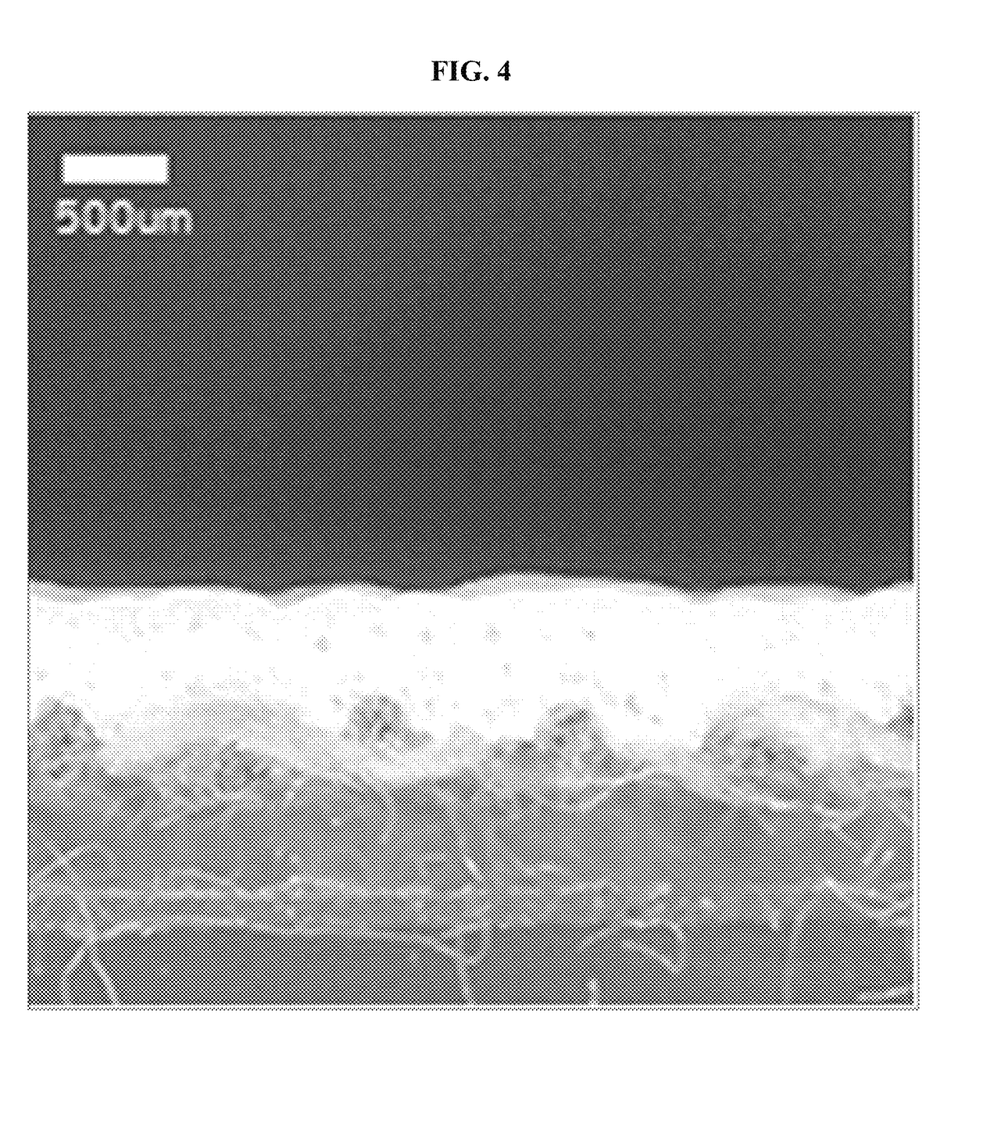
FIG. 4 is a magnified photograph showing that the oil-dispersed composition according to Comparative Example 1, which is applied to artificial leather four times, and then the application thickness is measured.
Figure 5:
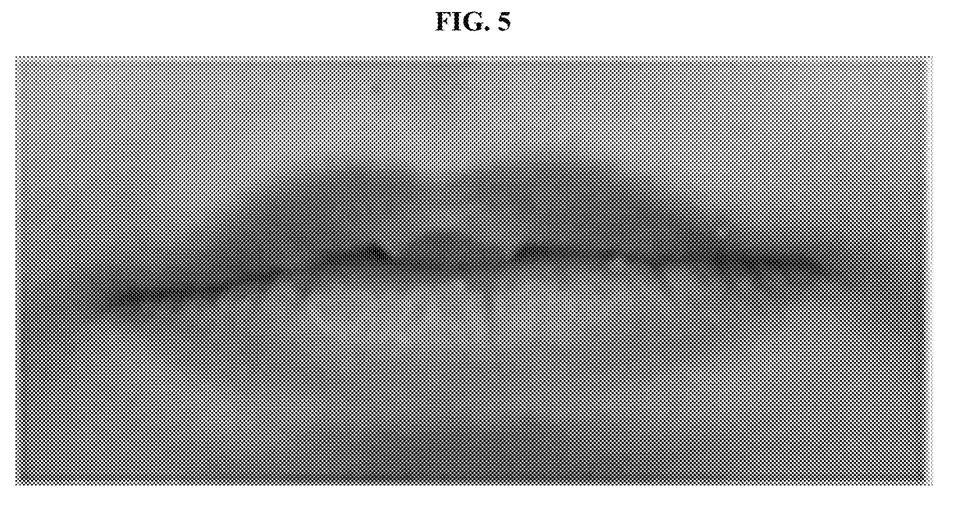
FIGS. 5 to 7 are photographs for confirming the redness, volume, elasticity, and density of the lips before applying the oil-dispersed composition according to Example 1 to the lips.
Figure 6:
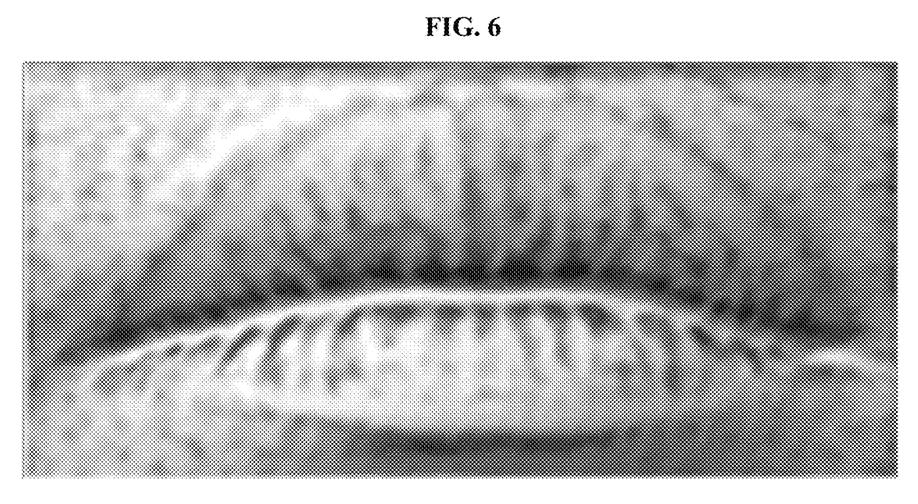
Figure 7:
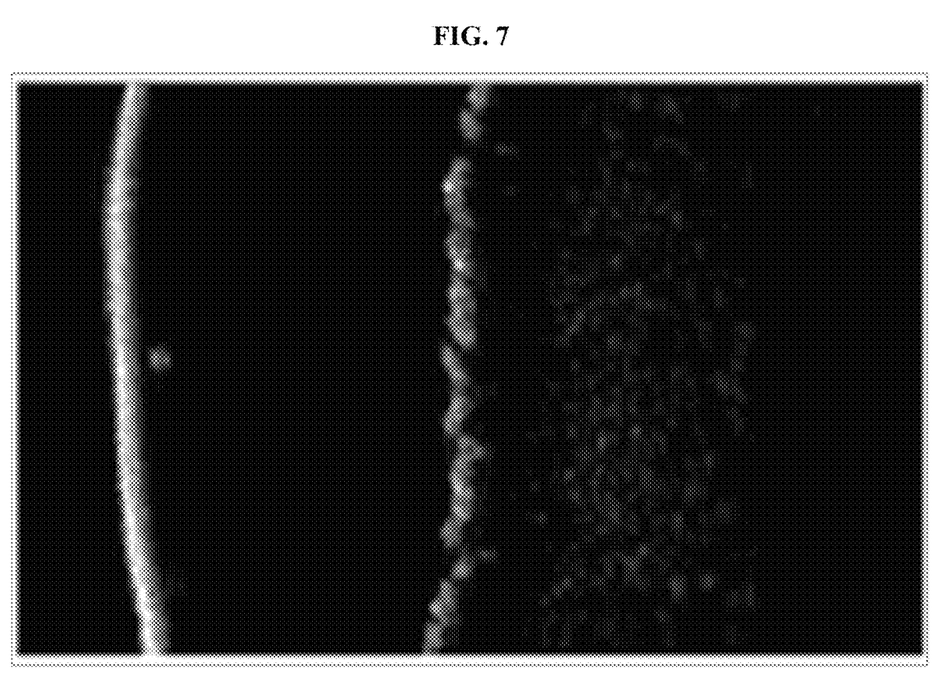
Figure 8:
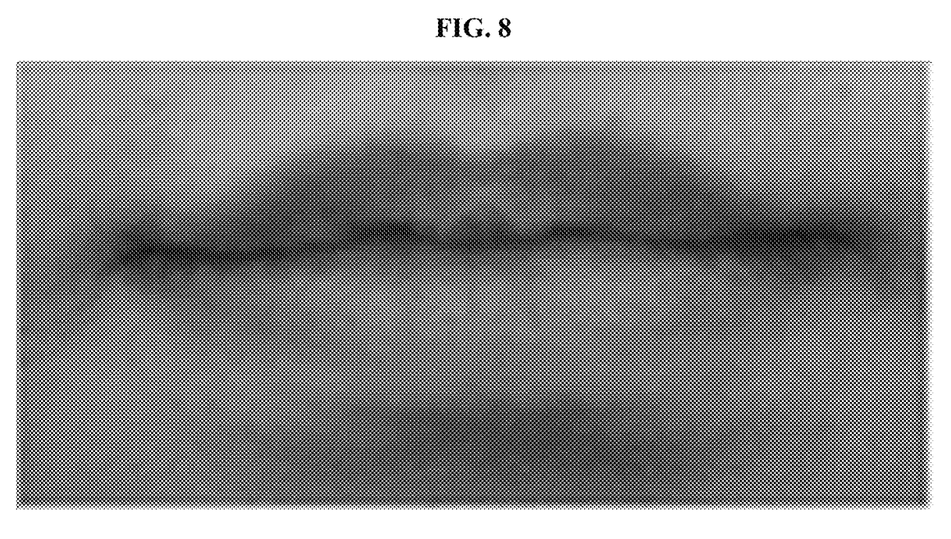
FIGS. 8 to 10 are photographs for confirming the redness, volume, elasticity, and density of the lips of the lips in 2 weeks after applying the oil-dispersed composition according to Example 1 to the lips.
Figure 9:
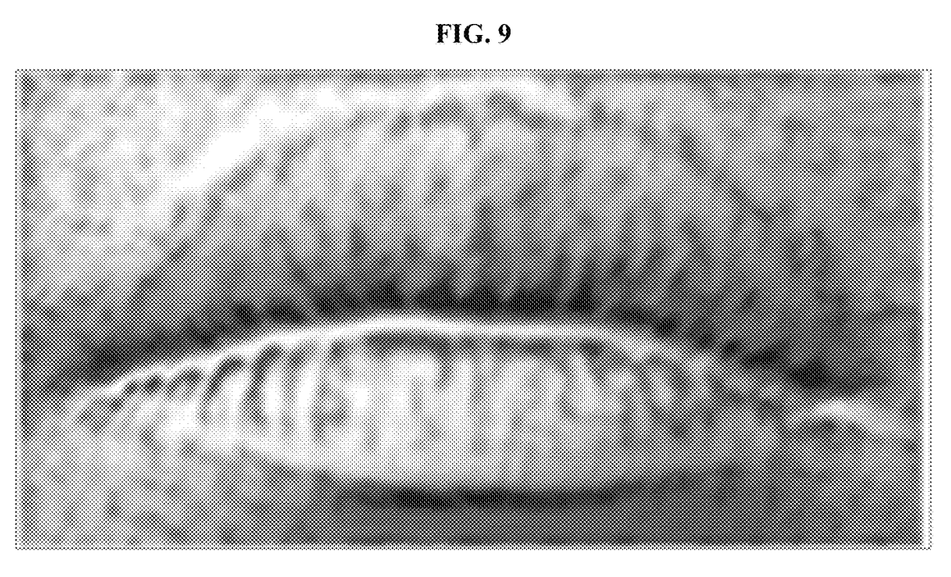
Figure 10:
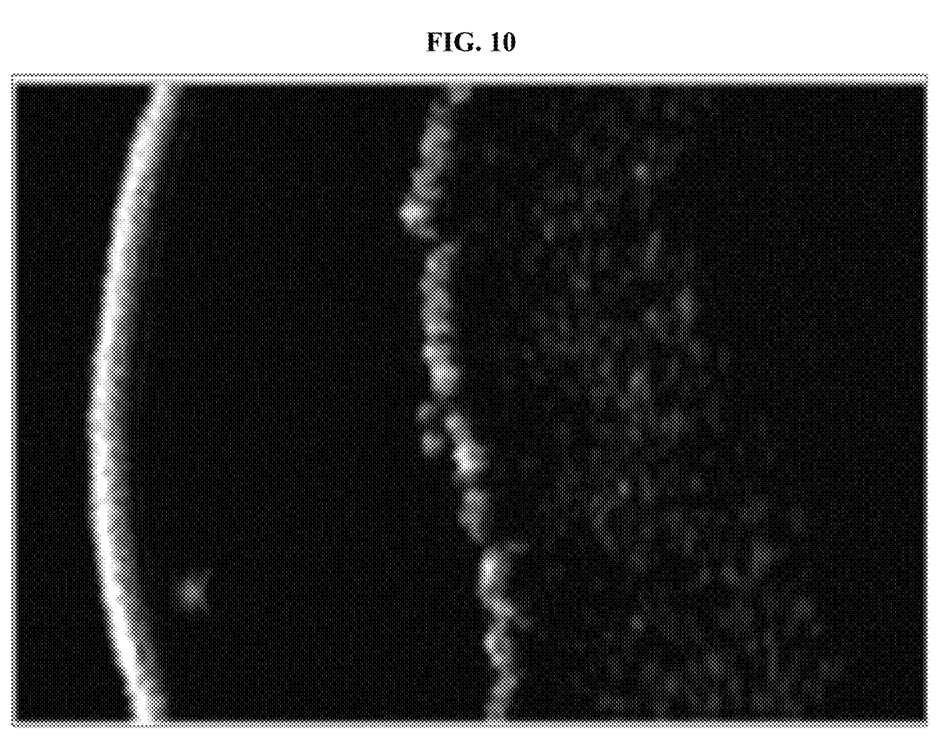

The oil-dispersed compositions according to Example 1 and Comparative Example 1 were respectively four times applied to an artificial leather, and then, each applied thickness was measured through a magnifying glass, and the results are shown in FIGS. 3 and 4.

Referring to FIGS. 3 and 4, the oil-dispersed composition according to Example 1 had a thickness of about 100 μm (FIG. 3), when 4 times applied, but the oil-dispersed composition according to Comparative Example 1 had a thickness of about 50 μm (FIG. 4), when 4 times applied, and accordingly, the oil-dispersed composition according to an embodiment had a larger thickness, even when the same number of times applied.

Evaluation 2: Measurement of Lip Care Effect

The oil-dispersed composition according to Example 1 was taken photographs before and 2 weeks after applied on the lips, and the results are shown in FIGS. 5 to 10 and Table 3. A magenta effect (or an effect of improving clarity of the lips) was considered to be obtained, when a redness value of the lips was 1% or more (when increased by 1% or more after the application, compared with before the application).

TABLE 3

| | Before application | 2 weeks after application | Increase/decrease rate (%) |
|---|---|---|---|
| Redness (a) | 28.83 | 29.264 | 1.505 |
| Volume (mm²) | 0.1156 | 0.1558 | 34.775 |
| Elasticity (R2) | 0.4889 | 0.533 | 9.02 |
| Density | 4 | 5.6 | 40 |

Referring to Table 3 and FIGS. 5 to 10, the oil-dispersed composition according to an embodiment exhibited improved volume, elasticity, and density through lip care as well as redness.

Evaluation 3: Measurement of Viscosity at High Temperature

Figure 11:
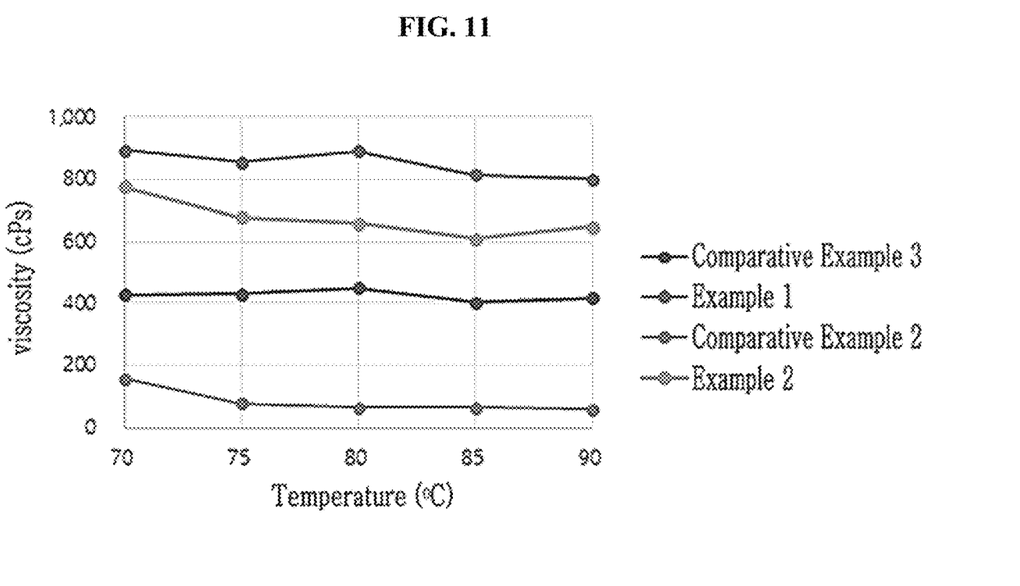
FIG. 11 is a graph showing changes in viscosity according to temperature of oil-dispersed compositions according to Example 1, Example 2, Comparative Example 2, and Comparative Example 3.

The oil-dispersed compositions according to Examples 1 and 2 and Comparative Exampled 2 and 3 were measured with respect to viscosity changes depending on a temperature by using Brookfield Thermosel, and the results are shown in FIG. 11. Specifically, the viscosity was measured after 5 minutes' waiting, when a corresponding temperature was reached (Spindle No. 18, 1 rpm).

Referring to FIG. 11, the oil-dispersed composition according to an embodiment maintained high viscosity at a high temperature of 70° C. In particular, when an ethylene/propylene/styrene copolymer and a butylene/ethylene/styrene copolymer as a thickener were used with a paste, the effect of maintaining high viscosity at a high temperature was much more improved.

Evaluation 4: Potency According to Dispersibility Generated During High-Temperature Filling In order to evaluate potency of the oil-dispersed compositions according to Examples 1 and 2 and Comparative Example 2, colored pearls were added to the oil-dispersed compositions (in order to visually check a degree of dispersion through the colored pearls) and then, allowed to stand in an 80° C. high temperature chamber for 1 hour. Then, photographs thereof were taken, and the results are shown in FIG. 12.

Figure 12:
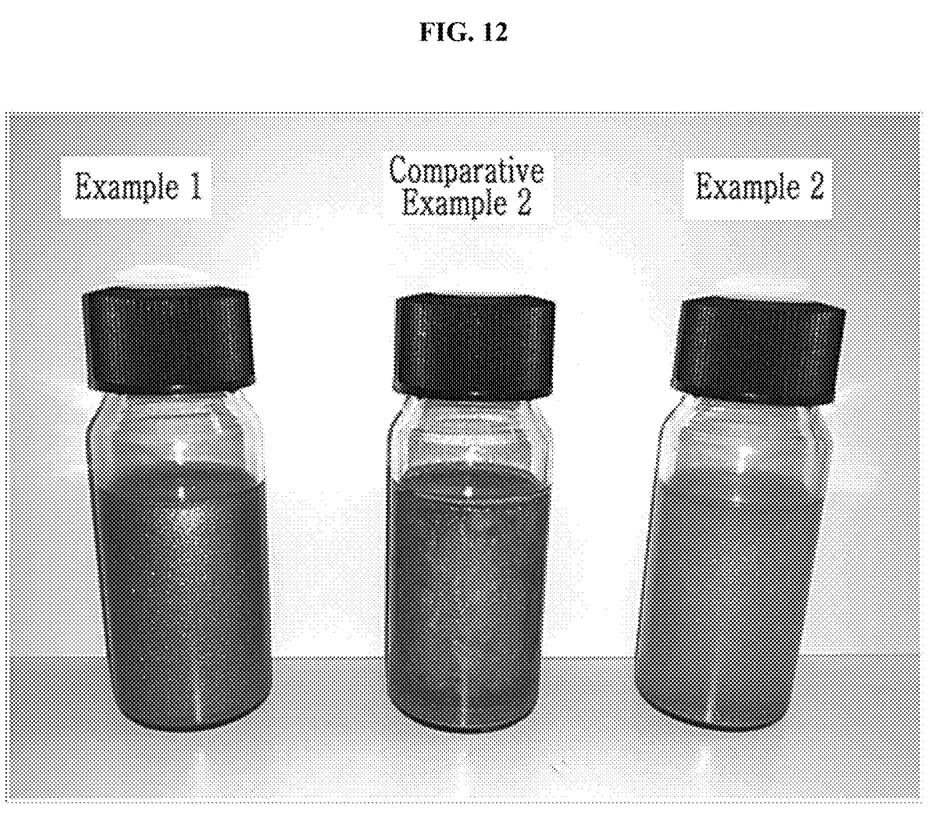
FIG. 12 is a photograph showing after adding colored pearls to the oil-dispersed compositions according to Example 1, Example 2, and Comparative Example 2, and leaving them in a chamber at 80° C. for 1 hour.

Referring to FIG. 12, since the colored pearls were uniformly dispersed in the oil-dispersed compositions according to an embodiment, the oil-dispersed compositions according to an embodiment might solve the potency problem at a high temperature. As for the oil-dispersed composition according to Comparative Example 2, the colored pearls a lot sank at the bottom, and the oil-dispersed composition according to Example 2 exhibited a slight layer separation but overall uniformly dispersion of the colored pearls. The oil-dispersed composition according to Example 1 exhibited uniform dispersion of the colored pearls.

While this invention has been described in connection with what is presently considered to be practical example embodiments, it is to be understood that the invention is not limited to the disclosed embodiments. On the contrary, it is intended to cover various modifications and equivalent arrangements included within the spirit and scope of the appended claims.

What is claimed is:

1. An oil-dispersed composition, comprising
   a water-soluble material comprising thymol trimethoxy cinnamate, a vitamin derivative, a ceramide, or a combination thereof,
   an ester oil comprising a glyceryl group-containing ester oil and an isostearyl group-containing ester oil,
   a paste comprising a polybutene, a hydrogenated polyisobutene, a phytosteryl/isostearyl/cetyl/stearyl/behenyl dimer dilinoleate, a dimer dilinoleyl hydrogenated rosinate, or a combination thereof, and
   a thickener comprising an ethylene/propylene/styrene copolymer, a butylene/ethylene/styrene copolymer, dextrin palmitate/ethyl hexanoate, glyceryl behenate/eicosadioate, or a combination thereof,
   wherein the paste and thickener are included in an amount of greater than or equal to about 30 wt % based on a total amount of the oil-dispersed composition, and wherein the glyceryl group-containing ester oil consists of polyglyceryl-2 triisostearate and the isostearyl group-containing ester oil consists of diisostearylmalate in which the isostearyl group-containing ester oil is included in an amount greater than that of the glyceryl group-containing ester oil.

2. The oil-dispersed composition of claim 1, wherein the paste is included in an amount greater than that of the thickener.

3. The oil-dispersed composition of claim 2, wherein the paste is included in an amount of greater than or equal to about 25 wt % based on the total amount of the oil-dispersed composition.

4. The oil-dispersed composition of claim 1, wherein the oil-dispersed composition further comprises waxes, butters, or a combination thereof.

5. The oil-dispersed composition of claim 1, wherein the oil-dispersed composition further comprises a hydrocarbon-based oil.

6. The oil-dispersed composition of claim 5, wherein the hydrocarbon-based oil comprises a hydrogenated poly(C6-14 olefin).

7. The oil-dispersed composition of claim 3, wherein the oil-dispersed composition comprises about 0.01 wt % to about 1 wt % of the water-soluble raw material, about 15 wt % to about 69 wt % of the ester oil, about 25 wt % to about 74 wt % of the paste, and about 0.1 wt % to about 10 wt % of the thickener, based on the total amount of the oil-dispersed composition.

8. The oil-dispersed composition of claim 1, wherein the oil-dispersed composition further comprises tocopherol, evening primrose oil (*Oenothera biennis* oil), or a combination thereof.

9. A method for treating skin of a subject, comprising applying the oil-dispersed composition of claim 1 to the skin.

10. A lip care cosmetic comprising the oil-dispersed composition of claim 1.

* * * * *